United States Patent [19]
Ellis

[11] Patent Number: 4,641,540
[45] Date of Patent: Feb. 10, 1987

[54] BULK MATERIAL SAMPLING APPARATUS

[76] Inventor: Jack J. Ellis, 2453 Indian Tree Run, Glencoe, Mo. 63038

[21] Appl. No.: 729,523

[22] Filed: May 1, 1985

[51] Int. Cl.⁴ ............................................. G01N 1/20
[52] U.S. Cl. ............................................... 73/863.53
[58] Field of Search ........................ 73/863.53, 864.32

[56] References Cited

U.S. PATENT DOCUMENTS

| | | | |
|---|---|---|---|
| 1,135,796 | 4/1915 | Hiller | 73/863.53 |
| 2,228,351 | 1/1941 | Hartshorn | 83/11 |
| 2,495,944 | 1/1950 | Pletta et al. | 73/423 |
| 2,977,800 | 4/1961 | Jordison | 73/423 |
| 3,541,862 | 11/1970 | Jordison | 73/423 |
| 3,791,218 | 2/1974 | Pennington | 73/864.32 |
| 3,875,803 | 4/1975 | Clewlow | 73/423 |
| 4,215,579 | 8/1980 | Hines et al. | 73/863.53 |
| 4,326,425 | 4/1982 | Gundersen et al. | |

OTHER PUBLICATIONS

Bluck, "High-Speed Sampling Cutters and Their Effect on Bias", Journal of Testing and Evaluation, vol. 7, No. 6, Nov. 1979, pp. 338–343.
Ramsey Engineered Sampling Systems, pp. 4, 5, 6, 7, Rev. 12/79.

Primary Examiner—Stewart J. Levy
Assistant Examiner—Robert R. Raevis
Attorney, Agent, or Firm—Gravely, Lieder & Woodruff

[57] ABSTRACT

Apparatus for extracting one or more individual samples from a free falling stream of bulk material by a suitable cutter that traverses the falling stream of the bulk material to collect a test sample and move it to a point where the sample can be delivered into a crusher and mixer-feeder for preparing the crushed material for handling to obtain therefrom a final quantity that is suitable for being subjected to a process whereby information characteristic of the bulk material may be determined.

15 Claims, 13 Drawing Figures

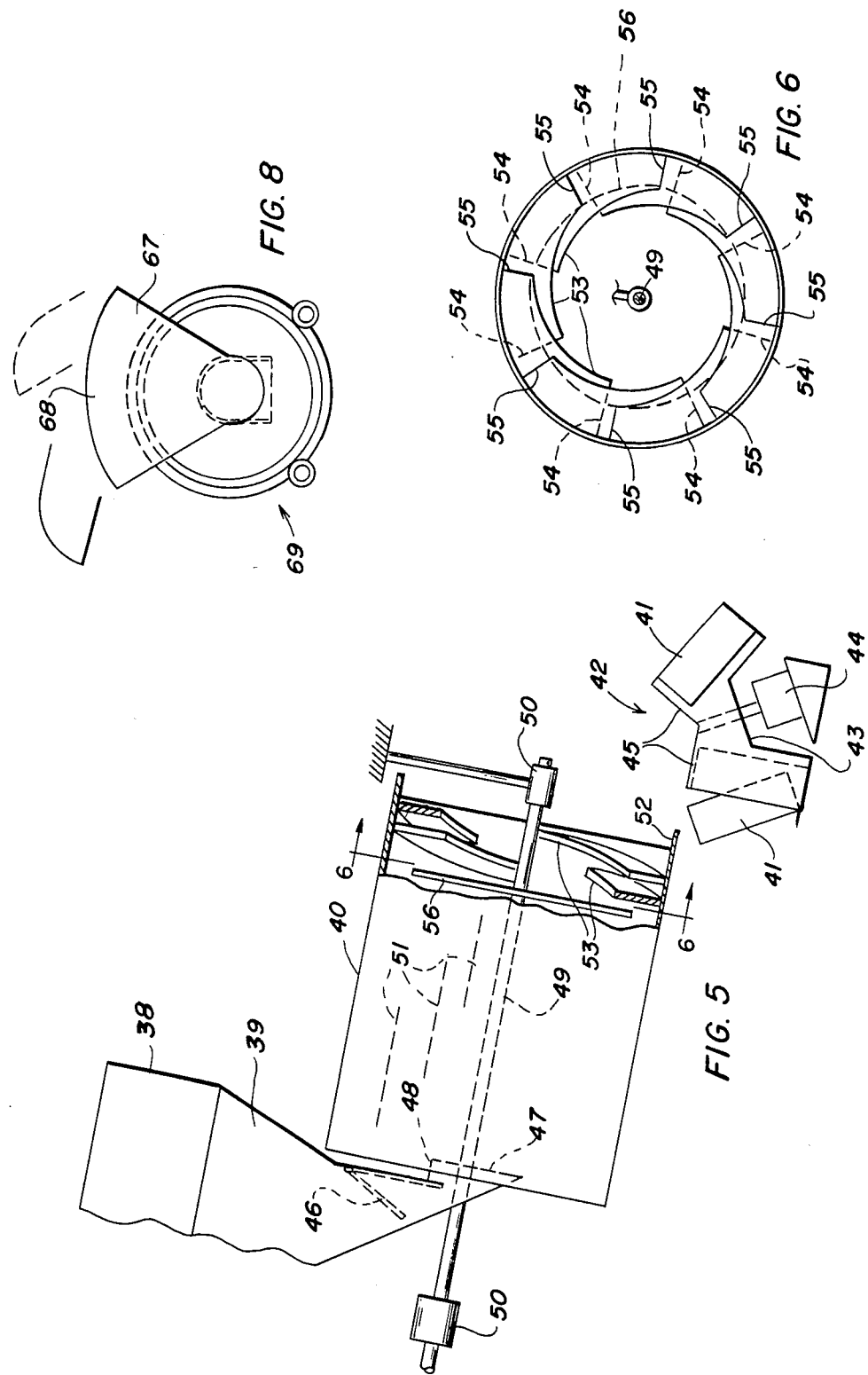

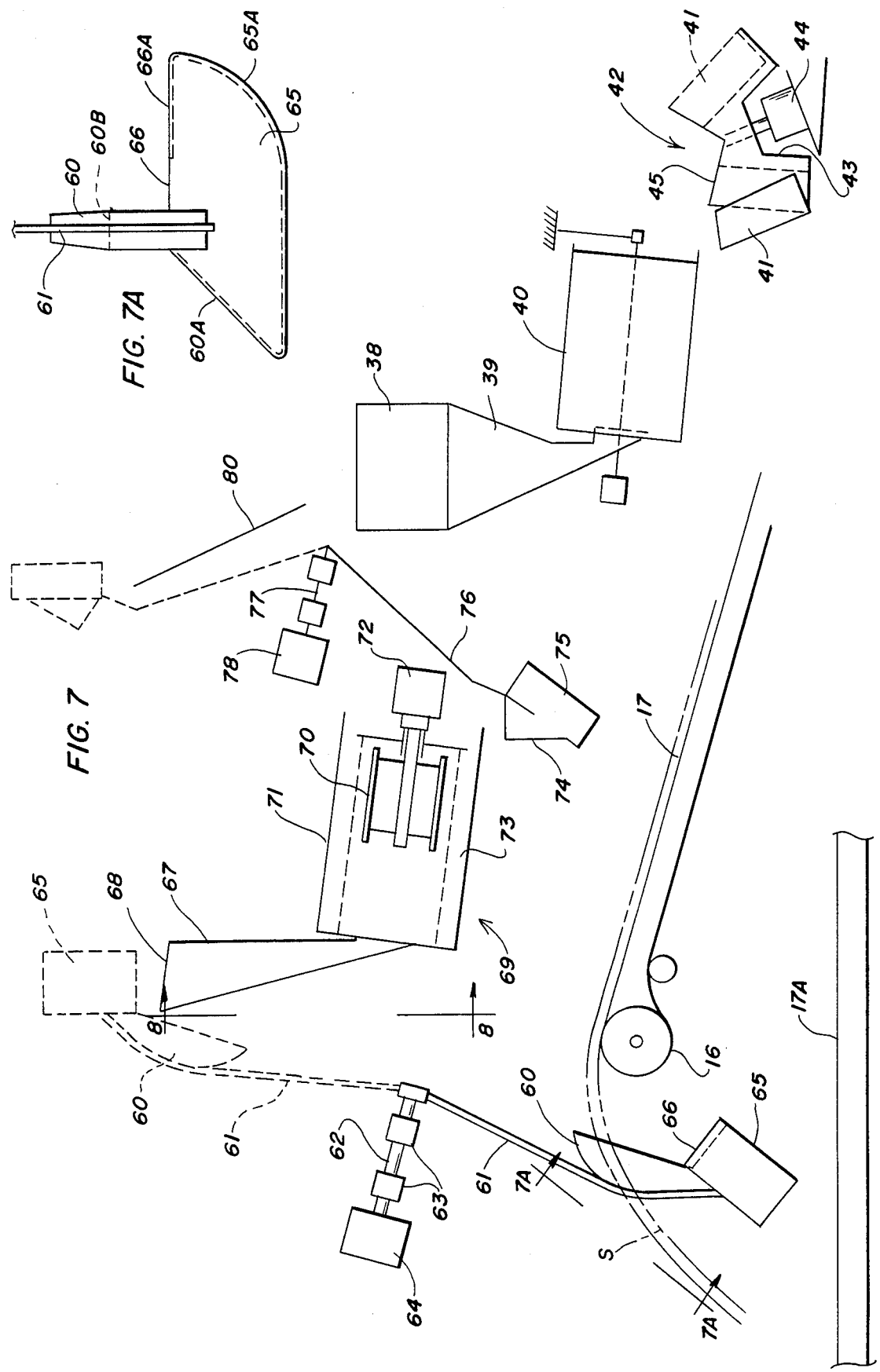

BULK MATERIAL SAMPLING APPARATUS

BACKGROUND OF THE INVENTION

1. Field of the Invention

This invention is directed to apparatus for cutting out of a stream of bulk material, or precrushed coal, a sample and, in a series of steps, securing further fractions of the original sample, a final one of which is then analyzed for important characteristics.

2. Description of the Prior Art

In actual practice of the art of coal sampling it is observed that apparatus for performing that task has depended upon a tower structure which is designed to initially elevate a lot or quantity of coal to the upper reach of the tower and allow it to fall by gravity into sampling devices. The problem with these installations is that expensive structure is required and coal elevating means is used to move reject coal to a discharge conveyor. In addition, the structure is so complicated that field erection is required and that adds cost to the final installation.

Efforts have been made to reduce the size of coal sampler structures. An early coal sampling apparatus conveyed the coal to an elevated position for establishing a free falling stream from which samples could be extracted and processed using flow guiding mechanism and auxiliary conveyors. Such an arrangement is shown in Pletta et al U.S. Pat. No. 2,495,944 of Jan. 31, 1950. This was followed by sampler mechanism employing complicated sample collector motion that was circular for collecting a sample and linear to dump the sample at a location removed from the margin coal stream. Reference is made to Jordison U.S. Pat. No. 2,977,800 of Apr. 4, 1961. An effort to improve on Jordison is disclosed in Clewlow U.S. Pat. No. 3,875,803 of Apr. 8, 1975 where instead of moving the sampler in a linear direction to a dump position, the sampler merely swung to a set position after making a sample cut through a falling stream, and a discharge chute was moved up to collect the sample and direct it into a collection chute. A somewhat similar sampler for bulk material is shown in Jordison U.S. Pat. No. 3,541,862 of Nov. 24, 1970. In this latter apparatus the sampler moved in a fixed curved guide to cut a sample from a free falling stream and deliver it to a fixed position chute where the sample was released to a chute.

A somewhat similar approach to sampling bulk material is disclosed by Gundersen et al U.S. Pat. No. 4,326,425 of Apr. 27, 1982. In this arrangement, a sampler bucket must be rotated while being swung in a curved path so it will only cut a sample in one direction of its passage through the falling stream. The bucket is required to rotate after its arrival at a dump station so its sample can be spilled into a chute and directed to processing means.

The foregoing prior art sets forth disclosures of complicated arrangements of structure which greatly increases the cost and entails a system of controls for achieving the dumping of the sample after it has been collected. There is a more serious problem in the prior art and that is the sample collecting means is required to pass through the stream of material twice but only collecting or cutting out a sample on one pass which means that the stream is disturbed during the non-collecting pass and the material in the stream is scattered at that time.

BRIEF DESCRIPTION OF THE INVENTION

The object of the present invention is to provide a coal sampling system that is capable of securing a desired and reasonable sample of coal from a predetermined quantity that meets normal requirements representative of that predetermined quantity. In practice the predetermined quantity of coal may vary in sizes of lots from less than one thousand tons to in excess of twenty thousand tons.

Another object of the present invention is to provide means that can obtain reasonable size final samples to be tested of about thirty pounds coal from free falling streams that vary from less than one hundred tons per hour to more than ten thousand tons per hour.

Still another object is to provide a coal sampling system that is able to secure the foregoing reasonable sample of the order of about thirty pounds when the system apparatus functions in any phase of the wide ranges of lot sizes and coal flow rates.

The objects of the present invention may be carried out in several arrangements of apparatus which include two, three or more stages of sampling the coal flow and feeding the samples through one or several crushing stages that finally reduce the samples to a tertiary sample as the last step.

A further object is to provide an automatic mechanical sampling system capable of securing a representative sample of material and reduce the quantity to an amount that an operator can remove and handle with ease. This must be accomplished when the lot of material sampled may have a top size classified as large as 6" or more and the quantity may exceed ten thousand tons. In order to accomplish these objectives normally there are two or three stages of sampling and one or two states of crushing. The top size of the normal sample provided for testing purposes by the sampling-system is ⅜", 4 mesh or 8 mesh and the weight may be thirty pounds or more.

The present invention embodies alternate apparatus arrangements which satisfy specific applications of coal sampling, depending on factors which involve uniform coal feed rates and minimum height of structure to reduce head room or where a cost efficient arrangement is suitable for non-uniform coal feed rates, or where the sample gathering bucket keeps the coal in a state of motion and provides a very uniform feed rate in a highly depending manner.

The reasons for gathering samples of coal from a moving flow of coal are generally governed in accordance with applicable standards. In addition the sampling systems must be operable under widely varying settings, sample cutter widths, cutter speeds and frequencies of cuts to reduce the initial size of cut to about thirty pounds of coal. The top size of coal in a given lot, the lot size and flow rate all go into determining when it becomes necessary to go from a system having two stages of sampling to a three stage system. When, however, it is only necessary to provide two sampling stages, the second sampler's main function is as an elevator and there may be multiple buckets rotating continuously in a given orbit to achieve the desired results. When three sampling stages are required, the second stage becomes a sampler as well as an elevator and it may have only one bucket operating on a predetermined time cycle.

Another important feature of this invention is that none of the sampling systems employ any form of mixing. A very few have hoppers and material is accumulated but not intentionally mixed. Another problem is that many three stage systems are set up to obtain fewer tertiary increments than secondary and some secondary increments are lost (not sampled).

The rotary mixer feeder accumulates secondary increments and may mix secondary increments collected from several primary increments before discharging. The discharge rate can be adjusted by the rate of rotation of the drum and the burden gate height limiting the amount of material entering the vanes and the angular tip of the drum.

BRIEF DESCRIPTION OF THE DRAWINGS

A presently preferred embodiment of the invention is illustrated in the accompanying drawings, wherein:

FIG. 5 is an enlarged and partly sectioned and partly schematic view of one component in the embodiment of FIG. 1;

FIG. 6 is an end view of the component of FIG. 5 showing outlet control plates as seen at line 6—6 in that FIG. 5;

FIG. 7 is a schematic view of a modified embodiment of bulk material sampling apparatus;

FIG. 7A is a view of the bucket detail seen along line 7A—7A in FIG. 7;

FIG. 8 is a fragmentary end view of the chute seen along line 8—8 in FIG. 7;

DETAILED DESCRIPTION OF THE EMBODIMENTS

Figure 1:
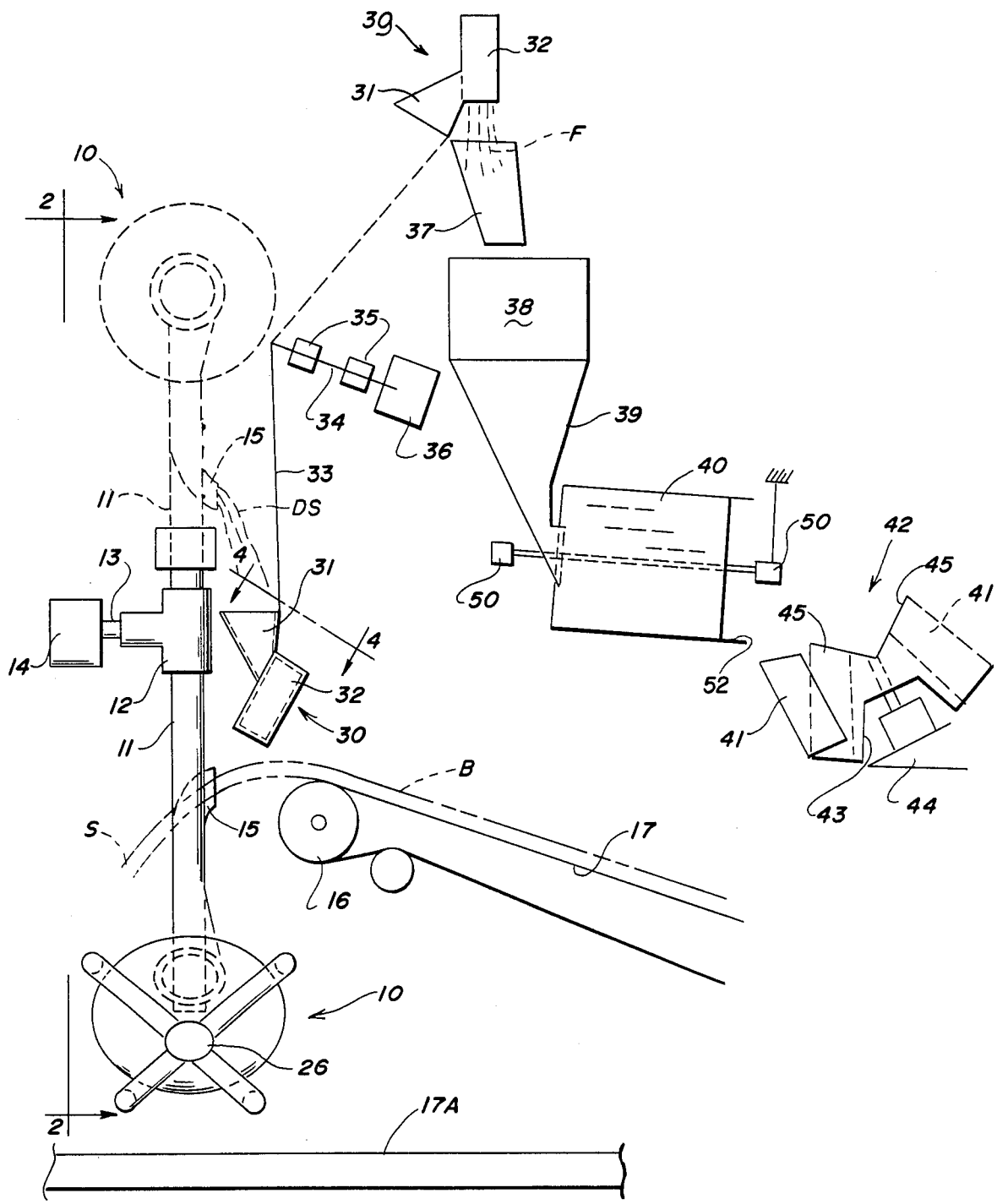
FIG. 1 is a general elevational view of a preferred embodiment of bulk material sampling apparatus, with some portions thereof disclosed in full line detail.
Figure 2:
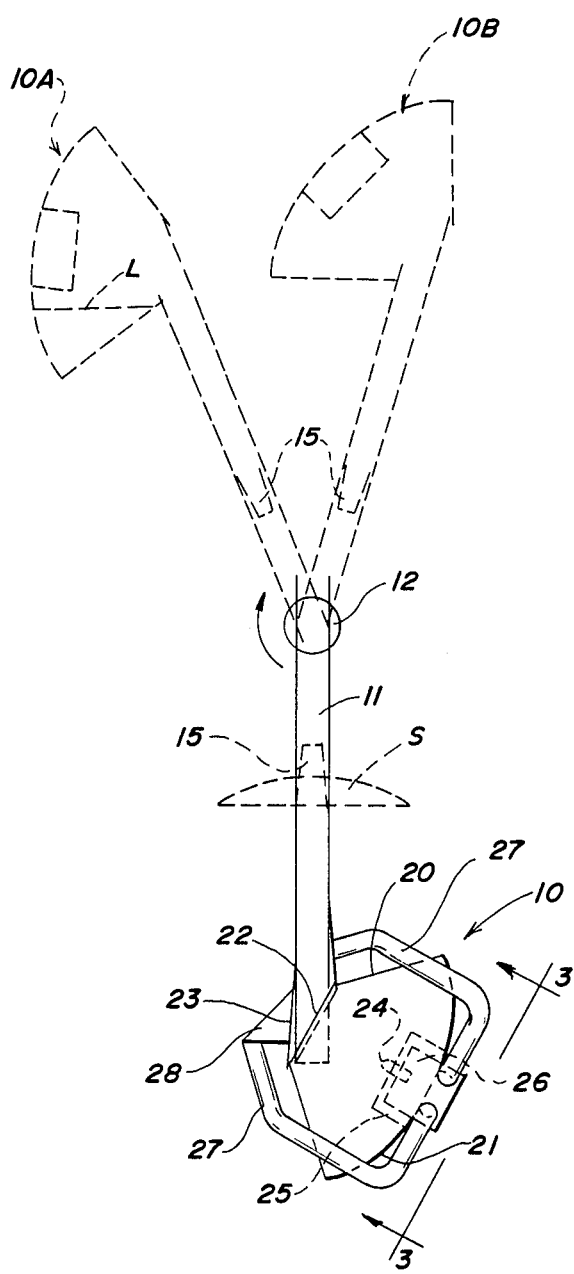
FIG. 2 is a schematic view of the embodiment of FIG. 1 as seen from another position along line 2—2 to disclose further details.
Figure 3:
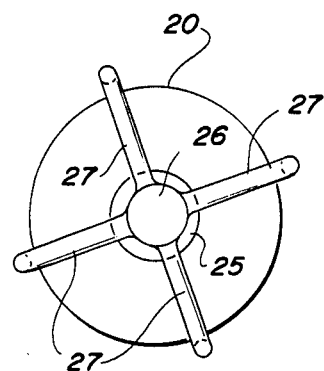
FIG. 3 is a view taken at line 3—3 in FIG. 2.

A first or preferred embodiment of apparatus, as seen in FIG. 1 comprises a primary sample collecting bucket 10 carried on a hollow arm 11 suitably counterweighted at 11A, and having a pivot hub 12 for the drive shaft 13 powered by a suitable prime mover 14 which can be a speed controllable electric gear motor capable of rotating the bucket 10 in a closed path about the axis of shaft 13. The arm 11 is hollow and connects with cutter 15 in position to receive a primary sample of the bulk material B from the primary flow thereof, all of which is projected off the head pulley 16 of a belt conveyor 17. The material B is projected into a free falling stream S at the elevation of the cutter 15 and what is not sampled continues in the primary flow 17A below. The material B is directed by the cutter 15 and hollow arm 11 in to the bucket 10, and is carried upwardly to a position where the collected sample is discharged. On comparing FIG. 2 with FIG. 1 it can be understood, due to the tilt of the bucket 10, that the path of movement of the bucket is transversely of the direction of the stream S, and such movement about the axis of the shaft 13 is clockwise.

The primary sample collecting bucket 10 has a conic side wall 20 closed at the large end by a curved bottom wall 21, and open at a circular inlet 22. The end portion of the hollow arm 11 enters the inlet at an angle and has one side cut away so it is open to the interior of the bucket. Since the inlet opening 22 is round and the arm 11 is a rectangular box, it is necessary to employ a tapering collar 23 to enclose the arm 11 and cover the circular inlet 22. A feature of the bucket is that it is rotated through its driven shaft 24 projecting into a recess 25 which receives a prime mover 26 connected to the shaft 24. The prime mover 26 is supported in operative position by bracket arms 27 which pass around the bucket wall 20 and attach to a suitable bracket 28 secured to the collar 23. Thus, the bucket 10 is able to rotate relative to the collar 23 and the arms 27. Electrical connections to the prime mover 26 (not shown) are supported by one arm 27 and the hollow arm 11 to reach connection at the hub 12.

During the orbiting movement of the bucket by the prime mover 14 about the axis of shaft 13, the bucket 10 also is rotated by the prime mover 26. The orbiting motion about the axis of shaft 13 (FIG. 2) carries the bucket upwardly through positions 10A and 10B during which the collected primary sample is discharged back through the cutter 15. During the bucket 10 travel from positon 10A through about 25° to position 10B the cutter 15 is substantially positioned so the primary sample being discharged is effectively directed into the path of travel of a second sample collector means 30 (see FIG. 1) which traverses an angle substantially equal to the angle included between positions 10A and 10B of the bucket 10. The second sample collecting means 30 travels in a clockwise direction, and is formed with a sample cutter 31 opening into a collector bucket 32.

During the rotation of the primary bucket 10 by the prime mover 14, the collected sample is concentrated in the trailing space of the bucket, and is discharged back through the arm 11. The speed of rotation of the bucket 10 and the motion about shaft 13 will cause the sample to be rolled out from the initial level L at a substantially uniform rate and not in a great rush that could temporarily clog the arm 11. The direction of rotation of the bucket 10 may be either clockwise or counterclockwise, but as shown it is clockwise.

Figure 4:
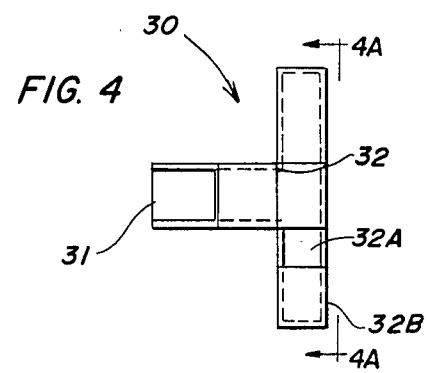
FIG. 4 is a top view of a second sample cutter and collector means appearing in FIG. 1 along line 4—4.
Figure 4A:
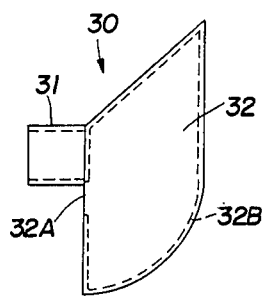
FIG. 4A is a side view in elevation of the sample cutter seen in FIG. 4 along line 4A—4A.

Continuing to refer to FIG. 1, the second sample collector means 30 is moved by its arm 33 (shown only schematically) about a shaft 34 carried in bearings 35 and driven in a clockwise direction (as noted in FIG. 2) by a third prime mover 36. In FIG. 4, the second sample collector means 30 is shown with a cutter 31 projecting from a collector bucket 32. The bucket 32 is formed with an outlet opening 32A. In the position of the collector means 30 at the lowest position in FIG. 1 only the cutter 31 is presented in open position to the discharging stream DS (FIG. 1) from the primary bucket 10. As the bucket 3.2 is moved to its upside down position, the sample collected therein will be released through outlet 32A in a flow F onto a guiding chute 37. The second collected sample will normally be concentrated in the bucket 32 at the bottom 32B (FIG. 4).

The flow F from the bucket 32 is directed by chute 37 into a suitable crushing mill 38, and the crushed sample is passed through to the outlet hopper 39. From hopper 39, the crushed sample is directed into a rotary mixer-feeder 40, and eventually a portion of the sample is released into one of several containers 41 carried in a container indexing device 42. The device is made up of a frame 43 rotatable on an axis tilted at an angle and rotated intermittently by a prime mover 44. The frame has a suitable cover 45 to close off the containers 41 after each container has been returned from its exposed sample receiving position. The capacity of each container may be about thirty pounds or more.

With reference to FIGS. 5 and 6, the hopper 39 of the mixer-feeder 40 is provided with a damper or gate 46 which is moved into a position closing off the hopper outlet 47 that opens into the inlet 48 of the mixer-feeder 40. The gate is opened momentarily when coal is not being crushed to discharge the crushed material that has collected over the gate into the mixer-feeder. The purpose of the gate is to prevent air flow through the crusher during crushing to minimize any change in moisture content of the material and minimize dust loss. In addition, when the contents of the mixer-feeder 40 is being discharged the gate 46 is in its closed position. The mixer-feeder 40 is operably carried on a shaft 49 supported in bearings 50, and a prime mover (not shown) is connected to shaft 49. The shaft of the mixer-feeder is tipped to facilitate the flow of material through the device. The interior of the mixer-feeder 40 is provided with stirring and lifting fins 51 on its interior wall. The outlet end 52 of the mixer-feeder 40 is provided with an internal arrangement of spaced control vanes 53 seen in greater detail in FIG. 6. In this example there are eight vanes. Each vane 53 has a first edge 54 that is set inwardly and under-lapped relative to a second edge 55 of an adjacent vane. The shaft 49 carries a flow restrictive plate 56 that controls the depth of the material entering between the vanes 53. In the view of FIG. 6 if the mixer-feeder rotates in a clockwise direction the vane ends 54 will push the material through the outlet end 52. When rotated counterclockwise the ends 54 cut into the material and direct it between the vanes so the trailing ends 55 push the material backwardly. As referred to in FIG. 1 the material pushed by the vanes 53 outwardly is collected in a container 41.

It is important to understand that the arrangement of components making up the assembly of FIG. 1 is to align them over the bulk material conveyor 17 so that uncollected or rejected portions of the samples of material being transferred from bucket 10 to bucket 30, and from the mixer-feeder 40 to a container 41 will fall back into the flow of the material on conveyor 17.

OPERATION OF THE PRIMARY EMBODIMENT

Material to be sampled, as before noted, is conveyed on a belt conveyor 17 and is discharged into free fall at the head pulley 16. While the material is in free fall cutter 15 travels through the stream at a uniform angular velocity, and the sides of the cutter are tipped to intersect the center of rotation 12. The increment obtained falls into rotating bucket 10. The cutter and bucket continue to swing around shaft 12 to the near vertical position. At the same time bucket 10 rotates about itself driven by gear motor 26. The material tumbles in the rotating bucket and the surface tends to seek a level position as illustated at 10A in FIG. 2. The material is discharged continuously and uniformly as the shaft rotates from position 10A to 10B.

The primary cutter 15 swings through the main stream of material numerous times during the sampling of the lot of material depending on the lot size and the aggregate of all of the primary increments (primary sample weight) which normally run less than 1% of the lot weight. Each primary increment is completely discharged from the rotating bucket 10 before the next increment is secured. The primary increment feedout period runs from less than 1 minute to in excess of 5 minutes.

The second sample collecting means 30 has a cutter 31 and bucket 32 which passes through the free fall stream F at a uniform angular velocity and the bucket discharges the material through the discharge port 32A into the crusher chute 37 and into crusher 38.

Several second sample increments are collected by means 30 for each primary sample collected by means 10 and there may be several sample collecting means 30 attached to shaft 34. The total amount of increments of material collected by the second means 30 may run from 10 to 100% of the primary sample. The crusher 38 discharges material into hopper 39. Some crushers may create or generate air flow that can change the moisture content of the material and create dust loss. An air tight gate 46 (FIG. 5) is closed during the crushing process. It blocks air movement while crushed material is accumulated in the hoper 39. Between crushing cycles the gate 46 is opened allowing the material to slide through outlet 47 and into rotary mixer-feeder 40.

The rotary mixer-feeder 40 is supported by its shaft 49 that is mounted in bearings 50. The inside of the drum contains mixing and lifting paddles 51. The mixing paddles 51 are designed to move the material laterally along the slightly tipped axis of the drum. Furthermore, the lifters 51 are designed to prevent sliding on the inside of the drum and make the material tumble down over itself. Rotating in one direction the means 40 is a mixer as the overlapping vanes 53 prevent material from discharging. When the means 40 rotates in the opposite direction material feeds out between the vanes 53 and the device continues to mix material.

The rotary mixer-feeder 40 will accumulate many secondary increments mixing them together and will then feed them out. The means 40 may not completely discharge except at the end of the run of a lot. The mixing cycle will be the longest duration and may exceed 80% of the time.

The tertiary sampler indexer 42 (see FIG. 5) is a series of containers 41 mounted on a rotating table 43 driven by a gear motor 44. The top of each container has cutting edges that extract a sample increment of the free falling stream from the rotary mixer, the rest falls back to conveyor 17.

Normally, one container 41 is tipped out during the sampling of the lot and when material is discharging the table will oscillate the container through the stream but the rotary velocity will be uniform when the cutter edges are in the stream. When a container 41 is tipped in, it is sealed against the underside of plate 45. The cutting edges are on radius lines from the center of turning of the table when the cutting edges on the container are in the tipped out position.

A modified embodiment of a bulk material sampler is shown schematically in FIG. 7. A primary sample cutter 60 is supported by an arm 61 from a shaft 62 carried in bearings 63. A prime mover 64 drives the shaft 62 to move the cutter 60 through the falling stream S of bulk material. The cutter 60 directs a sample of the bulk material into a bucket 65 which has an outlet in the wall 66 much like that seen in FIG. 4 relative to bucket 32. As the bucket 65 moves through its upper path the sample material will be discharged into a chute 67. The chute is fan-shaped (see FIG. 8) so its upper end 68 includes an angle of about 50° to register with the arc of travel of bucket 65. The chute 67 directs the sample into a combined rotary feeder-crusher 69 in which the crusher component 70 is cantelevered into the lower end of the rotating drum 71 from a prime mover 72. An internal screen 73 is employed to control the size of the sample particles allowed to discharge so it can be discharged and sampled by a second cutter 74 from a bucket 75. The cutter 74 and its bucket 75 is supported by an arm 76 from a driven shaft 77 of a prime mover 78. As the bucket 75 moves through its upper path, the sample material is discharged onto and directed by a chute 80 into an assembly of components 38 to 42 of the character referred to and disclosed in FIG. 1, and it is not believed to be necessary to describe it again. Furthermore, the cutter 74 and attached bucket 75 are a substantial duplicate of the cutter 31 and bucket 32 seen in FIG. 1.

The primary sample cutter 60 and its collecting bucket 65 of FIG. 7 are seen in greater detail in FIG. 7A. In that detailed view the bucket 65 has flat side walls, one being seen in the drawing and joined by a slanted end wall 60A angularly directed away from the sample cutter 60 attached to the support 61. The bucket 65 has a curved bottom wall 65A which joins the angular wall 60A to a flat upper wall 66A, and the latter wall is formed with an outlet opening 66 adjacent the sample cutter 60. The cutter 60 is open between its outer end and the dotted line margin 60B so that sample material entering the inlet will be directed into the bucket 65. As the bucket moves upwardly the sample material will move along the curved wall 65A and form in the corner area between the walls 65A and 66A. Continued movement to its top position (FIG. 7) will cause the sample to flow through the outlet 66 as the bottom wall 65A becomes the top wall.

Figure 9:
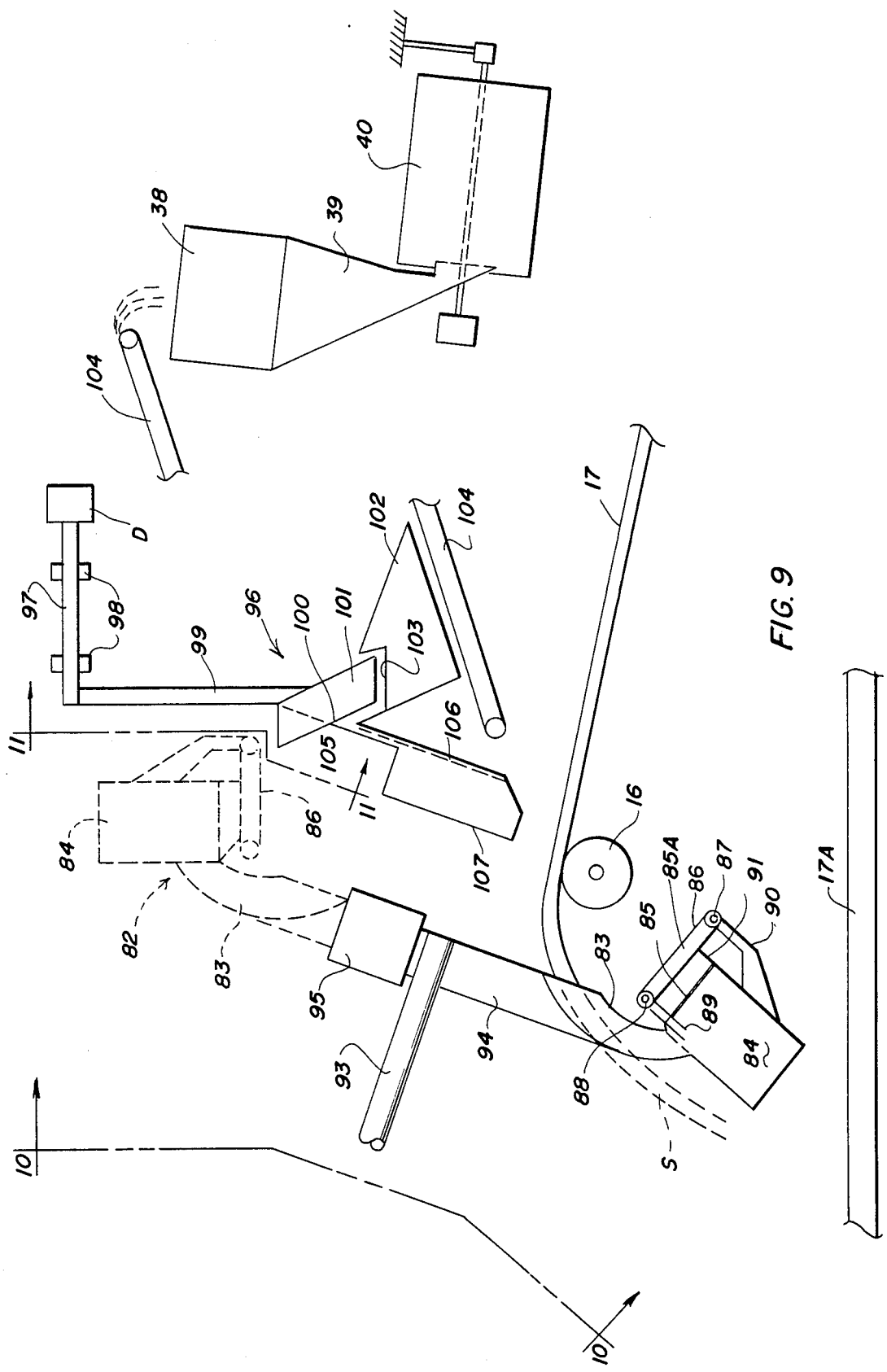
FIG. 9 is a fragmentary view of a modified sample cutter and collecting bucket equipped with a conveyor belt feeder.

What is shown in FIG. 7A is exemplary of the shape of the bucket 32 in FIG. 1 except that the sample cutter 31 is more funnel shaped. Also, the bucket shape of FIG. 7A is exemplary of the bucket 75 in FIG. 7. The only difference is that the cutter 74 is funnel shaped to catch the falling material. What has been shown in FIG. 9 is a sample collecting bucket 84 having the shape of the bucket 65 in FIG. 7A and a cutter 83 like that seen at 60 in FIG. 7. However, the outlet from bucket 84 is open to the belt 86.

FIG. 9 discloses a modified cutter and bucket assembly 82 for obtaining a primary cut of material from the free falling stream S in the primary flow. In this assembly, the cutter portion 83 is curved so its entrance will be in position to receive a sample of the material as it crosses the path of the stream. The sample so cut is deposited in the bucket 84, as indicated. The bucket is provided with an outlet in the wall 85, the outlet being shrouded by a flexible skirt 85A. The bucket 84 is intended to be similar to the bucket seen in FIG. 7A, but is equipped with a discharge belt 86 mounted on rollers 87 and 88 supported by suitable brackets 89 and 90 from the bucket 84. A drive motor (not shown) is provided to drive the roller 87 so the belt 86 carries the sample discharged to the secondary cutter 101 seen in FIG. 11. A burden depth gate 91 is positioned to control the amount of material released off the end of the belt 86 for sampling by the secondary sampler mechanism. The drive for belt 86 can be combined with the roller 87 in known manner in the conveyor art. The provision of primary cutter and bucket assembly 82 will provide a substantially uniform feed with a minimum of head room requirement.

Figure 10:
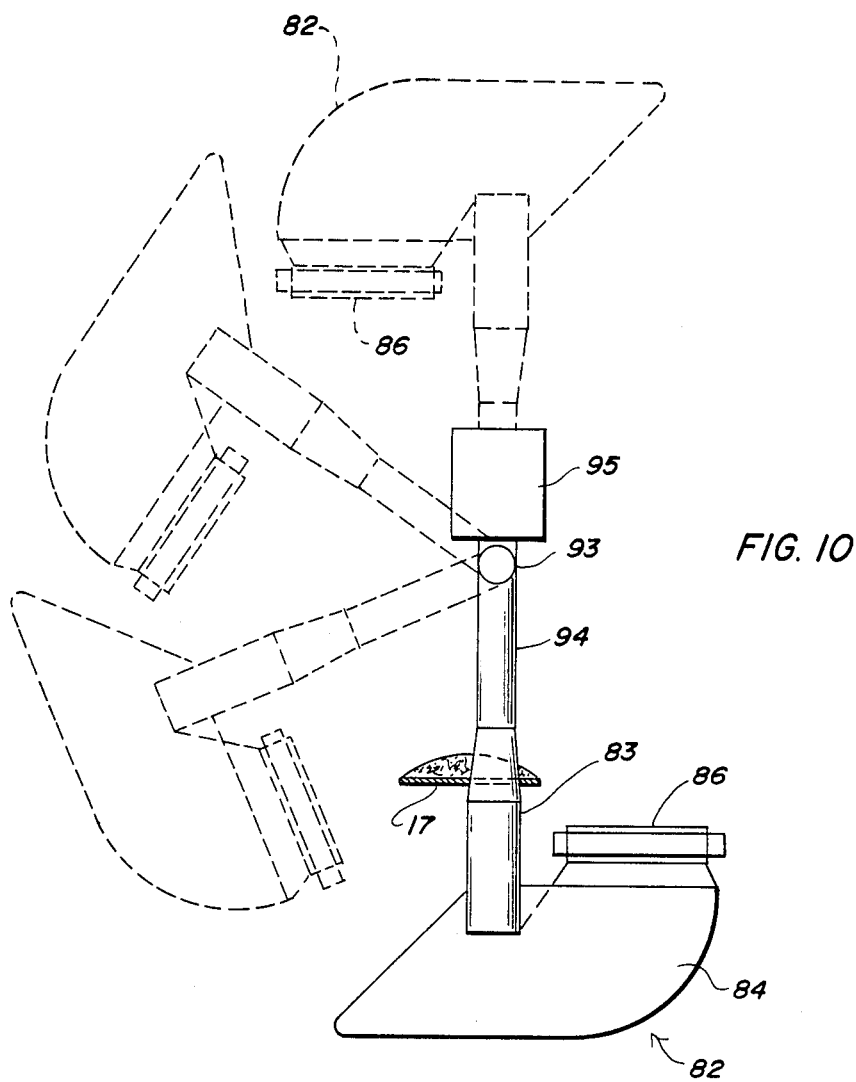
FIG. 10 is a view seen along line 10—10 in FIG. 9.
Figure 11:
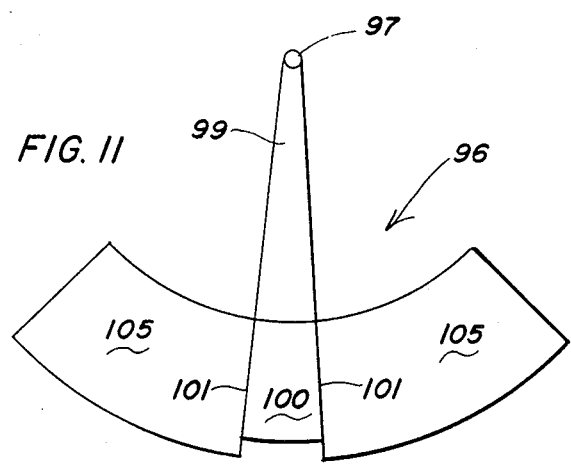
FIG. 11 is a view seen along line 11—11 in FIG. 9.

The assembly 82 of FIG. 9 is illustrated schematically in FIG. 10 in several positions of movement about the axis of shaft 93 which is connected to the assembly 82 by arm 94 having a suitable counterweight 95 to balance the single assembly 82. As that assembly passes through and across the flow of bulk material, a sample is collected in the bucket 84, and as the bucket moves upwardly to the top position in FIG. 10 the sample is shifted along the curved side of the bucket until it is caught by the belt 86. At the top position the bucket 84 stops moving and the belt 86 is driven to discharge the same in a substantially even flow dictated by the burden gate 91. The sample is discharged to a second sampling device 96, the details of which are seen in FIGS. 9 and 11.

The second sampler 96 includes a rock shaft 97 operated by a suitable drive D. The shaft supported by bearings 98 connects to an arm 99 which extends down past the belt feeder 86. The lower end of arm 99 carries a secondary sample cutting chute 100 having sides 101 to confine the sample falling into the chute 100 so it will enter a stationary guide 102 having a notch 103 to allow the chute 100 to swing through the guide 102. The secondary sample cutter 100 swings through the material discharged by the belt 86 in each direction of its pendulous movement and directs the sample into the guide chute 102 which directs it onto a belt conveyor 104. The material not sampled by chute 100 falls onto deflector wings 105 which extend outwardly at each side of the chute 100 to direct the rejected material to return it onto the bulk feed belt 17. This function occurs at each side of chute 100, and each wing 105 directs the rejected material onto the outer slanting surface 106 of the guide chute 102. That surface 106 is framed by sides 107 to confine the reject flow so it returns to the primary feeder belt 17. During the discharging of the primary sampling bucket 84, that bucket is stopped at the top position seen in FIG. 10. This then allows the rejected material to return to the primary flow on belt 17 before the primary sampler assembly 82 returns to its bottom position for again sampling the flow. This avoids "salting" the samples.

In order to include other components in the view of FIG. 9, portions of the conveyors 17 and 17A have been omitted so the silhouette of a crusher and mixer-feeder assembly similar to the assembly seen in FIG. 1 can be included. Furthermore it can be appreciated that the secondary sample cutting chute 100 may be operatively supported from the bottom or lower end by a suitable shaft set so it is substantially parallel to the conveyor 104. This arrangement would result in the top end of the chute 100 moving through an arc that would be the opposite of the arc seen in FIG. 11, but an equivalent for obtaining a sample of the material being discharged from the bucket 84. It is therefore understood that the view of FIG. 11 would be reversed so the shaft 97 would be below the chute 100, and the wings 105 would be curved down.

SAMPLING SYSTEM EXAMPLES

The utility of the system of FIG. 1 can be illustrated in connection with an assumed consignment of a coal allotment of four thousand tons which is being conveyed by the belt conveyor 17 at a rate of two thousand tons per hour. A suitable final sample of that allotment is assumed to be about thirty pounds. Let it be understood that the conveyor 17 is moving the allotment of coal in bulk at about two thousand tons per hour with the top size at about two inches. The material is to form that four thousand ton consignment. The primary cutter 15 has a width of about 6" to sample the 2" top size coal and travels at a speed of 18" per second which will secure about three hundred seventy pounds per cut. The cutter 15 needs to make 70 cuts.

The rotating drive arrangement of the collecting bucket 10 is one that keeps the collected material in continual motion and will provide very uniform material feed rates in a highly dependable manner. The rotary bucket is believed to be ideal as a uniform, trouble free, feeder to a secondary sampler. Sampling requirement calls for the primary cutter 15 and bucket 10 to cut out seventy primary cuts each weighing about three hundred seventy pounds, a total of twenty-six thousand, or about 13.0 tons of coal. The primary sampler must obtain an increment of three hundred seventy pounds every 103 seconds, and each increment must be discharged from the bucket 10 before another one is collected. It is arbitrarily assumed that the bucket 10 can be emptied in about 80 seconds in order to get an empty bucket back to the free falling stream S in 103 seconds. At that rate of discharge the sample discharged is about 277.5 pounds per minute.

The secondary sampling by means 30 to obtain six secondary cuts for each primary cut will require six secondary cutters 31 and buckets 32 all rotating on the common shaft 34. However, FIG. 1 only shows two for simplifying the drawings. Furthermore, the cutter 15 and its bucket 10 traverses through the bulk material stream S and secures an increment of the material which is elevated to a location where it is discharged and subject to a second sampling. In this stage the reject material is returned to the conveyor 17 by gravity fall and without need for any conveying equipment. After being crushed the second sample is released to a rotary mixer-feeder which can discharge it at a substantial uniform rate of flow to be sampled a third time in a final cutter and indexing device 42. From the device 42 the sample is run through a processing cycle which is not a part of the present disclosure.

The embodiment of FIG. 7 includes three stages of sampling and two stages of crushing, with the first crusher being combined in a rotary feeder.

The bucket 65 seen in the embodiment of FIG. 7 is an economical design that is believed to be ideal when a uniform feed rate is not required, as when feeding a crusher or mixer-feeder. Its utility is well adapted for use with a primary crusher and on a secondary sampler that feeds a crusher.

The bucket assembly 82 of FIG. 9 illustrates a design combined with a conventional belt feeder and burden depth gate for providing a uniform feed with a minimum use of head room. However, all forms of buckets are especially desirable as they require a minimum use of head room.

RESUME

The objective of a coal sampling system is to secure a reasonable quantity of coal that represents a total consignment of coal. A reasonable quantity for a man to handle is about thirty pounds, however, it can be as small as two pounds of coal and still represent the total consignment. The size of a consignment can vary from less than one thousand tons to in excess of twenty thousand tons and the coal flow rates can range from less than one hundred tons per hour to more than ten thousand tons per hour. Then in order to secure this reasonable quantity of coal (thirty pounds) with these wide ranges of lot sizes and coal flow rates it becomes necessary to design sampling systems that may have as little as:

(a) a primary sampler, crusher and secondary sampler (two stages of sampling, one of crushing)

(b) a primary and secondary sampler crusher and tertiary sampler (three states of sampling and one of crushing).

(c) a primary sampler, primary crusher, secondary sampler, an tertiary sampler (three stages of sampling, two crushing).

Some systems have four stages of sampling. In addition these systems must be operated under widely varying settings, cutter widths, cutter speeds and frequencies to reduce the quantity of coal to about thirty pounds.

The top size of the coal, consignment size and coal flow rate all go into determining when it is necessary to go from a two stage to a three stage system with a conventional sampling system.

The proposed new systems all have three samplers. The first two not only sample the coal but elevate the material to a desirable elevation for further processing, then when it is only necessary to have two stages the secondary sampler's main function is to be utilized as an elevator and there may be multiple buckets rotating continuously to achieve the desired results. When three stages of sampling are required the secondary's function becomes a sampler and elevator and it may contain only one bucket and be operating on a timer.

Two examples will be illustrated. The first has moderate sampling requirements and is typical for the system to be described in Example No. 1. The second has larger sampling requirements and is typical for the system to be described in Example No. 2.

EXAMPLE NO. 1

Conditions: 4" Top Size—Raw Coal—1,200 tons/Hr—1,200 ton Lot Size
Primary: 12" Width—18"/sec.

$$\text{No. of Primary Cuts} = 35\sqrt{\frac{1{,}200}{1{,}000}} = 38 \quad \text{Say } \underline{\underline{40}}$$

$$\text{Frequency } \frac{60 \text{ min.} \times 60 \text{ sec/min}}{40} = \frac{3{,}600 \text{ sec.}}{40} = 90 \text{ seconds}$$

$$\text{Quantity } \frac{1{,}200 \times 2{,}000 \times 12}{3{,}600 \times 18} = 445 \text{ lbs/Primary}$$

Feedout Rate: Assume Primary should be fed out in 80 sec.

$$\text{Then } 445 \times \frac{60}{80} = 334 \text{ lbs/min. for 80 sec.}$$

Secondary: 12" cutter width; assume 8' radius on secondary circumference at cutter $= 2\cdot\pi R = 2\cdot\pi \times 8 \times 12 = 600''$ $$\text{Use 8 buckets operating continuously} = \frac{12'' \times 8}{600''} \times 100 = 16\%$$

Quantity of Secondary $$445 \times .16 = 71.2 \text{ lbs/primary}$$

$$334 \times .16 = 53.44 \text{ lbs/min.}$$

Crusher: to 4 mesh $$71.2 \text{ lbs} \times 40 = 2{,}848 \text{ lbs/Lot or } \frac{2{,}848}{60} =$$

$$48 \text{ lbs/min. (if continuous)}$$

Mixer-Feeder: Assume Feeds Out 20% of time $$\text{Feedout rate of mixer feeder is } \frac{2{,}848}{.20 \times 60} = 237 \text{ lbs/min. or}$$

237 lbs/min. for 12 min. (but not continuous)

Tertiary: Cutter width 1.5"—Cutter Speed 12"/sec.—60 cuts $$\text{Quantity} = \frac{237 \times 1.5}{60 \times 12} = .49 \text{ lbs/cut} \times 60 = 29.6 \text{ lbs/Lot}$$

EXAMPLE NO. 2

Conditions: 4" Top Size—Raw Coal—8,000 tons/Hr—8,000 ton Lot Size
Primary: 12" Width—18"/Sec.

$$\text{No. of Primary Cuts} = 35\sqrt{\frac{8{,}000}{1{,}000}} = 98.99 \quad \text{Say } \underline{\underline{100}}$$

$$\text{Frequency } \frac{60 \times 60}{100} = \frac{3{,}600}{100} \text{ sec.} = \underline{\underline{36 \text{ seconds}}}$$

$$\text{Quantity} = \frac{8{,}000 \times 2{,}000 \times 12}{3{,}600 \times 18} = 3{,}000 \text{ lbs}$$

Feedout Rate: Assume Primary should be fed out in 30 sec.

$$\text{Then } 3{,}000 \times \frac{60}{30} = 6{,}000 \text{ lbs/min.}$$

Primary Crusher: Crush to 1"
Secondary: 4" Cutter—18"/sec.—4 cuts per primary $$\text{Quantity } \frac{6{,}000 \times 4}{60 \times 80} = 22.2 \text{ lbs/cut}$$

One cut every 8 sec. or 4 cuts/primary $4 \times 22.2 = 88.8$ lbs/primary
Crusher to 4 mesh: $88.8 \times 100 = 8{,}8880$ lbs/Hr $= 148$ lbs/min.
Mixer-Feeder: Assume Feeds out 20% of time $$\text{Feedout rate of mixer-feeder is } \frac{8{,}800}{60 \times .20} = 740 \text{ lbs/min. or}$$

740 lbs/min. for 12 min. (but not continuous)

Tertiary: Cutter width 2"—cutter speed 8"/sec.—60 cuts $$\text{Quantity} = \frac{148 \times 2''}{60 \times 8''/\text{sec.}} = .617 \text{ lbs/cut} \times 60 = 37 \text{ lbs/Lot}$$

Primary Cutter

ASTM has a requirement of taking a minimum of from 20 to 35 primary increments for any size consignment of coal less than one thousand tons. The number of increments is based on whether the coal is washed or raw. For example, 20 increments are sufficient for washed coal while 35 are sufficient for raw coal.

If the quantity is in excess of one thousand tons then the number of increments is increased by the ratio of the square root of the tonnage. The minimum number of primary increments then for four thousand tons of raw coal would be:

$$35\sqrt{\frac{4{,}000}{1{,}000}} = 70 \text{ primary cuts}$$

Next, assuming the top size of the coal is 2", ASTM requires a cutter width of $2\frac{1}{2}$ to 3 times maximum particle size or say 6". Then, with a cutter speed of 18"/sec. and a material flow rate of two thousand tons per hour the amount of primary increment collected in one pass is calculated as:

$$\frac{2{,}000 \text{ tons/Hr} \times 2{,}000 \text{ lbs/ton} \times 6''}{3{,}600 \text{ sec./Hr} \times 18''/\text{sec.}} = 370 \text{ lbs.}$$

In as much as 70 increments are required and the minimum total time required to handle four thousand tons at two thousand tons/Hr is two hours, then the primary increment timing is:

$$\frac{2 \times 3{,}600}{70} = 103 \text{ sec.}$$

The entire primary cut must be fed out before the next one is secured so the primary feedout rate is arbitrary. It is established that the primary should be fed out in 80 seconds. Then the feedout rate is:

$$\frac{60}{80} \times 370 = 277.5 \text{ lbs/min.}$$

Secondary Cutter

If the primary increment is not crushed ASTM requires six secondary cuts per primary All primaries have a fixed feedout rate so in this example when the main stream feed rate is 50% or one thousand tons per hour, the amount of primary increment is ½ of maximum and the feedout takes one-half of the maximum time of 80 seconds.

The secondary frequency then is established at considerably more than 6 per primary at full stream flow in order to secure at least 6 when the flow is reduced.

In this example we have established that at maximum flow the primary would be fed out in 80 seconds, then at ½ flow the primary would be fed out in 40 seconds and to secure 6 secondaries the secondary cutter should secure a cut every 6 seconds. Then the coal is crushed and the top size to which the coal should be crushed is the subject of much discussion. When coal has a high percentage of surface moisture and is crushed to a small top size it can plug the sampling system and the sample may lose surface moisture.

Crushing in ASTM is classified to 8 mesh or 4 mesh but some of the newer systems crush to ⅜".

Tertiary

The frequency of the sampling stage after crushing either by the secondary or tertiary is also very loosely defined in ASTM. One interpretation that some sampling manufacturers use is a minimum of 60 increments for the final stage. This means that some of the secondaries in this example would not be sampled.

In this example there would be a minimum of 70×6=420 secondaries. Normally the number of tertiaries is adjusted to give the desired amount of sample weight.

There are more types of primary bucket designs and each one has a specific application depending on other factors. As an example, if there were no crushing between the primary and secondary it would be desirable to have a uniform and controlled feed rate to the secondary and the rotary bucket (FIG. 1) or belt feeder (FIG. 9) design would be utilized. Then if head room were a serious factor the belt feeder design would be selected.

If the primary cut were to feed to a crusher the more simplied bucket design would suffice.

In view of the foregoing disclosure of presently preferred embodiments as depicted in FIGS. 1, 7 and 9, it is to be understood that modifications in any of the arrangements may occur to those skilled in the art without departing from the principles of the invention which have been described herein. It should be pointed out that the drawings depicting various embodiments are necessarily presented in schematic form in order to simplify the drawings without sacrificing an adequate presentation of structure that can take many different forms depending on strength and load factors. However the present disclosure is intended to depict what are considered to be operative forms that may be carried out by those skilled in the art without restricting the apparatus to a certain direction of movement as it is understood that installation variables may take different forms.

What is claimed is:

1. Bulk material sampling apparatus for collecting a sample of the bulk material from a free falling stream, the apparatus comprising:

(a) conveyor means operable for moving bulk material in a primary flow having a free falling stream therein;

(b) primary sample collecting means movable between a position below said conveyor means and an elevated position above said conveyor means in one direction in a closed path which adjacent said position below said conveyor means intercepts the free falling stream of bulk material and collects a sample therefrom, said collecting means moving the sample of bulk material through said elevated position over said conveyor means and releasing the bulk material as it passes said elevated position above said conveyor means; and (c) sample collecting means adjacent said elevated position of said primary sample collecting means for receiving at least a portion of the bulk material released from said primary sample collecting means at said elevated position, the material uncollected by said primary sample collecting means returning to said primary flow.

2. Bulk material sampling apparatus as set forth in claim 1 wherein said primary sample collecting means is movable in a circular path about a fixed center.

3. Bulk material sampling apparatus set forth in claim 1 wherein said primary sample collecting means has an inlet in position for passing through the free falling stream, said inlet serving as the sample outlet in said elevated position of said primary collecting means.

4. Bulk material sampling apparatus set forth in claim 1 wherein said primary sample collecting means rotates concurrently with discharging this sample.

5. Bulk material sampling apparatus as set forth in claim 1 wherein said sample collecting means includes a bulk material crushing means positioned above said primary flow.

6. Bulk material sampling apparatus as set forth in claim 1 wherein said sample collecting means includes a bulk material crushing means having an inlet for receiving said at least a portion of the bulk material and an outlet for releasing material crushed therein, and other processing means receiving the crushed material from said outlet and positioned above said primary flow.

7. Bulk material sample apparatus as set forth in claim 1 wherein said sample collecting means includes primary sample crushing means for said at least a portion of the bulk material, said primary crushing means having an outlet; a rotary mixer-feeder having an inlet connected to said outlet of said primary sample crushing means and an outlet for the crushed material; and means for collecting crushed material discharged from said mixer-feeder outlet.

8. Bulk material sampling apparatus as set forth in claim 7 wherein a movable gate is operably disposed adjacent said primary sample crushing means outlet, reversible drive means is connected to said mixer-feeder, and discharge control means is disposed at said mixer-feeder outlet; said discharge control means releasing material from said mixer-feeder during only one direction of rotation thereof.

9. Bulk material sampling apparatus for collecting a sample of the bulk material from a free falling stream, the apparatus comprising:

(a) conveyor means in a first elevation for moving bulk material in a primary flow direction having a free falling stream therein;

(b) sample cutter means rotatable in a closed path about an axis above the first elevation of said conveyor means and aligned for cutting transversely through said free falling stream;

(c) bucket means carried by said sample cutter means for receiving a sample of bulk material cut from the free falling stream by said cutter, said bucket being movable with said sample cutter means about said cutter axis to a second elevation above said primary flow stream for discharging the sample in a second free falling stream; and (d) means operably mounted in a position for cutting a sample of bulk material from said second free falling stream at said second elevation, said operably mounted means being positioned above said primary flow stream such that bulk material missed by said sample cutting means returns to said primary flow by gravity in a free fall.

10. Apparatus for extracting individual samples of bulk material as it falls in a stream, said apparatus comprising:

(a) a sample collecting device having a collecting bucket and a cutter connected to said collecting bucket;

(b) means moving said sample collecting device in a closed path which at one point in said closed path passes through the stream of falling bulk material such that said cutter intercepts the stream of falling bulk material and directs the intercepted material into said collecting bucket, and at a second point in the closed path said bucket is inverted to discharge the bulk material therefrom;

(c) bulk material collecting means operable to receive the bulk material discharged from said inverted collecting bucket; and (d) other means for finally cutting out from the bulk material collecting means a test portion of the intercepted material.

11. The apparatus set forth in claim 10 wherein said collecting bucket rotates for discharging the bulk material at a substantially uniform rate.

12. The apparatus set forth in claim 10 wherein said other means includes a bulk material crusher and a feeder for receiving the crushed bulk material.

13. The apparatus set forth in claim 10 wherein said sample collecting device has said cutter open to said bucket at one side, said bucket has a curved bottom wall and a top wall with a sample discharge opening therein, such that upon bucket inversion the sample material passes through said discharge opening.

14. The apparatus set forth in claim 10 wherein said sample collecting device has a bucket 65 formed with an end wall 60A, a top wall 66A, and a bottom wall 65A connected to said end wall 60A and said top wall 66A, said cutter having a sample receiving inlet 60 and an outlet opening 66 from said bucket adjacent said end wall 60A to direct the sample between said end and bottom walls, said bottom wall having a portion thereof approaching said top wall 66A remote from said outlet opening 66 and at an angle for directing the sample collected therein toward said outlet opening.

15. The apparatus set forth in claim 10 wherein said sample collecting device includes a bucket 65 having a top wall 66A with an outlet opening 66, a bottom wall 65A curved to connect to said top wall 66A spaced from said outlet opening 66, and a sample cutter 60 opening to said bucket for directing a sample into said bucket, said outlet opening 66 being effective to discharge a sample upon said bucket being inverted.

* * * * *